US006626822B1

(12) United States Patent
Jaeger et al.

(10) Patent No.: US 6,626,822 B1
(45) **Date of Patent: *Sep. 30, 2003**

(54) IMPLANTABLE MICROPHONE HAVING IMPROVED SENSITIVITY AND FREQUENCY RESPONSE

(75) Inventors: Eric M. Jaeger, Redwood City, CA (US); Geoffrey R. Ball, Sunnyvale, CA (US); Duane E. Tumlinson, San Jose, CA (US)

(73) Assignee: Symphonix Devices, Inc., San Jose, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/615,414

(22) Filed: Jul. 12, 2000

Related U.S. Application Data

(63) Continuation of application No. 08/991,447, filed on Dec. 16, 1997, now Pat. No. 6,093,144.

(51) Int. Cl.[7] .......................... H04R 25/00; A61N 1/08

(52) U.S. Cl. ........................... 600/25; 381/326; 607/57

(58) Field of Search ........................... 600/23, 25, 483, 600/484, 515, 823; 181/128–137; 381/68, 326; 607/55–57; 434/112

(56) References Cited

U.S. PATENT DOCUMENTS

| | | | | |
|---|---|---|---|---|
| 2,702,354 A | | 2/1955 | Chorpening | |
| 3,736,436 A | | 5/1973 | Crites | |
| 3,938,615 A | | 2/1976 | Bodenger | |
| 4,281,222 A | | 7/1981 | Nakagawa et al. | |
| 4,524,247 A | | 6/1985 | Lindenberger et al. | |
| 4,591,668 A | | 5/1986 | Iwata | |
| 4,597,099 A | | 6/1986 | Sawafuji | |
| 5,085,628 A | | 2/1992 | Engebretson et al. | |
| 5,146,435 A | | 9/1992 | Bernstein | |
| 5,148,492 A | | 9/1992 | Uzawa et al. | |
| 5,303,210 A | | 4/1994 | Bernstein | |
| 5,329,593 A | | 7/1994 | Lazzeroni | |
| 5,452,268 A | | 9/1995 | Bernstein | |
| 5,624,376 A | | 4/1997 | Ball et al. | |
| 5,624,377 A | | 4/1997 | Davis | |
| 5,814,095 A | | 9/1998 | Muller et al. | |
| 5,859,916 A | | 1/1999 | Ball et al. | |
| 5,881,158 A | | 3/1999 | Lesinski et al. | |
| 6,093,144 A | * | 7/2000 | Jaeger et al. | 128/98.1 |

FOREIGN PATENT DOCUMENTS

| | | |
|---|---|---|
| JP | 54-133125 | 10/1979 |
| JP | 58-38098 | 3/1983 |
| JP | 6-225385 | 8/1994 |
| WO | WO 97/44987 | 11/1997 |

OTHER PUBLICATIONS

HNO—Hals–Nasen–Ohren–Heilkunde, Kopf–und Hals–Chirurgio, Preprint of Abstracts, "Fully Implantable Hearing Aid TICA LZ 3001 Product Summary", Oct. 1997, vol. 45, 5 pages total.

(List continued on next page.)

*Primary Examiner*—Eric F. Winakur
*Assistant Examiner*—Nikita R. Veniaminov
(74) *Attorney, Agent, or Firm*—Townsend and Townsend and Crew LLP

(57) ABSTRACT

Implantable microphone devices that may be utilized in hearing systems are provided. An implantable microphone device allows the implantable microphone's frequency response and sensitivity to be selected. A microphone device with an increased membrane flexibility and a decreased acoustic compliance of the sealed cavity. Vibrations of a membrane are transmitted through a primary air cavity and through an aperture of a microphone. Keeping a flexible membrane and decreasing the sealed air cavity compliance are the preferred way to simultaneously increase overall sensitivity of the device, and move the resonance peak to higher frequencies.

52 Claims, 8 Drawing Sheets

OTHER PUBLICATIONS

Schellin, R. et al. "Corona–poled piezoelectric polymer layers of P(VDF/TrFE) for micromachined silicon microphones," *J. Micromach. Microeng.*, Jan. 1995, vol. 5, pp. 106–108.

Scheeper, P.R. et al. "Improvement of the performance of microphones with a silicon nitride diaphragm and backplate," *Sensors and Actuators A*, 1994, vol. 40, pp. 179–186.

Deddins, A.E. et al. "Totally Implantable Hearing Aids: The Effects of Skin Thickness on Microphone Function," *Am. J. Otolaryngol.,* 1990, vol. 11, pp. 1–4.

Suzuki, Jun–Ichi et al. "Early Studies and the History of Development of the Middle Ear Implant in Japan," *Adv. Audiol.*, 1988, vol. 4, pp. 1–14.

Yanagihara, Naoaki, M.D. et al. "Develoment of an Implantable Hearing Aid Using a Piezoelectric Vibrator of Bimorph Design: State of the Art," *Otolaryngology Head and Neck Surgery,* Dec. 1984, vol. 92, No. 6 pp. 706–712.

Ohno, Tohru "The Implantable Hearing Aid, Part I," *Audecibel*, Fall 1984, pp. 28–30.

* cited by examiner

IMPLANTABLE MICROPHONE HAVING IMPROVED SENSITIVITY AND FREQUENCY RESPONSE

This application is a continuation of, and claims the benefit of priority from application Ser. No. 08/991,447, filed on Dec. 16, 1997, now is a U.S. Pat. No. 6,093,144, issued Jul. 25, 2000, the full disclosure of which is incorporated herein by reference.

BACKGROUND OF THE INVENTION

The present invention is related to hearing systems and, more particularly, to implantable microphone devices that may be utilized in hearing systems.

Conventional hearing aids are placed in the ear canal. However, these external devices have many inherent problems including the blockage of the normal avenue for hearing, discomfort because of the tight seal required to reduce the squeal from acoustic feedback and the all-too-common reluctance for hearing-impaired persons to wear a device that is visible.

Recent advances in miniaturization have resulted in the development of hearing aids that can be placed deeper in the ear canal such that they are almost unnoticeable. However, smaller hearing aids inherently have problems, which include troublesome handling and more difficult care.

Implantable hearing devices offer the hope of eliminating problems associated with conventional hearing aids. One requirement for a fully implantable hearing device or system is an implantable microphone.

All microphones necessarily contain an interface between the internal components and the environment in which it will be situated. For non-piezoelectric designs, air-conduction microphones utilize a membrane, which can be made of various materials, stretched or formed to varying tensions. The tension in the membrane has a first order effect on the response of the microphone. A highly stretched membrane will tend to resonate at a high frequency, with a flat response at frequencies below the resonance. However, a higher tension in the membrane will also tend to lower the sensitivity of the microphone.

Prior art implantable microphones for use with hearing systems have comprised an electret microphone disposed within an air cavity, enclosed by a stretched stainless steel membrane. The air cavity is hermetically sealed, necessitated by implantation in the body. The membrane is stretched tight and laser welded; the resulting system frequency response therefore has a low sensitivity and a sharp high frequency resonance peak. An improved device response would have high sensitivity, comparable to an electret microphone alone in air, and would be generally flat across the audio frequency, especially in the range of speech (500–4,000 Hz). Additional requirements for an improved implanted microphone include low distortion and low noise characteristics.

Traditional, non-implantable type microphones have an air cavity behind the membrane that is not sealed, with reference to the nearest surface behind the membrane. Traditional microphones are concerned with optimal membrane displacement, and typically have several air cavities which are used to influence the shape of the microphone response. An implantable microphone design that incorporates a membrane, enclosing a sealed chamber containing an electret microphone, is necessarily concerned with an optimal pressure build-up in the sealed cavity. This pressure build-up in turn displaces the membrane of the electret microphone. However, a sealed air cavity presents new challenges to the design and optimization of implantable microphones.

With the advent of fully implantable devices for stimulating hearing, there is a great need for implantable microphones that provide excellent audio performance. The present invention provides improved audio performance through improvement of microphone design.

SUMMARY OF THE INVENTION

The present invention provides implantable microphone devices that may be utilized in hearing systems, particularly in systems having bone mounted and other implantable drivers. The device comprises a flexible membrane disposed over a sealed cavity. The membrane may be made substantially flexible by etching or forming the membrane until it is very thin. Also, the sealed cavity may be limited to a very small volume which decreases the sealed air cavity acoustic compliance. Both of these examples simultaneously increase overall sensitivity of the device and move the damped resonance peak to higher frequencies.

In a preferred aspect an implantable microphone device is provided which comprises a housing and a membrane disposed over a surface of the housing to define a primary air cavity therebetween. A microphone assembly is secured within the housing. The microphone assembly has a secondary air cavity and an aperture which couples the secondary air cavity to the primary air cavity so that vibrations of the membrane are transmitted through the primary air cavity and aperture to the secondary air cavity. A microphone transducer is disposed in the secondary air cavity to detect said transmitted vibrations. Preferably, the microphone transducer comprises an electret membrane, a backplate, and electrical leads. Advantageously, a protective cover over the membrane is provided to protect the membrane from direct impact, where the protective cover is perforated to allow for free flow of vibration to the membrane.

In one configuration, the housing further includes a rear chamber. The rear chamber encases electric leads to the microphone, and provides external access to the leads through a hermetic feedthrough.

In yet another configuration, the membrane may comprise at least one compliance ring. Preferably, a plurality of compliance rings may be used. The compliance ring may be either etched or formed into the membrane or otherwise secured to it by any suitable means.

In a second aspect of the implantable microphone device, surface details are positioned on a surface of the housing. Preferably, the surface details may include pits, grooves, or at least one hole which connects the primary air cavity to a rear chamber of the housing. The surface details are provided to increase resonance peak damping.

In a third aspect, the implantable microphone comprises a housing comprising a rear chamber and includes a thin-walled tube section or other port opening for filling or evacuating specialty gases from said chamber. Filling the various cavities of the microphone with specialty gases decreases the acoustic compliance of those cavities. Accordingly, the housing further comprises a microphone assembly which may be vented, such that the gases can permeate each cavity of the implantable microphone. Alternatively, surfaces details on the housing, such as holes, may also connect the various cavities of the microphone device.

In a fourth aspect, the implantable microphone device, comprises a biocompatible material positioned proximate to the membrane. Preferably, the biocompatible material is biodegradable and degrades over time. Example materials include lactide and glycolide polymers. The position of the biocompatible material may vary from, for example, simple contact with only the front surface of the membrane to complete encapsulation of the entire microphone. This material provides protection from initial tissue growth on the microphone which may occur after implantation of the device. A volume occupying layer may be used to occupy a space between the membrane and an opposing surface of the biocompatible material. The volume occupying layer may naturally, over time, permanently fill up with body fluids or may comprise a permanent, biocompatible fluid-filled sack. In either form, these fluids will maintain an interface between the membrane and the surrounding tissue.

In a fifth aspect, the implantable microphone device comprises a microphone assembly with the secondary air cavity removed such that the electret membrane is directly exposed to the primary air cavity. The removal of the secondary air cavity creates a further reduction in overall air cavity volume which leads to a reduction in the acoustic compliance of the microphone.

In a sixth aspect, the implantable microphone device has a modified microphone assembly which eliminates the electret membrane. The assembly comprises an insulation layer secured on the inside surface of the implantable microphone membrane. An electret membrane-type material is, in turn, secured on the insulation layer. A backplate is disposed within the primary air cavity proximate to the insulation/membrane-type material combination. This aspect of the invention provides the advantage of a direct electret displacement, a lower overall component count, and an overall thinner microphone profile.

DETAILED DESCRIPTION OF THE PREFERRED EMBODIMENTS

Figure 1:
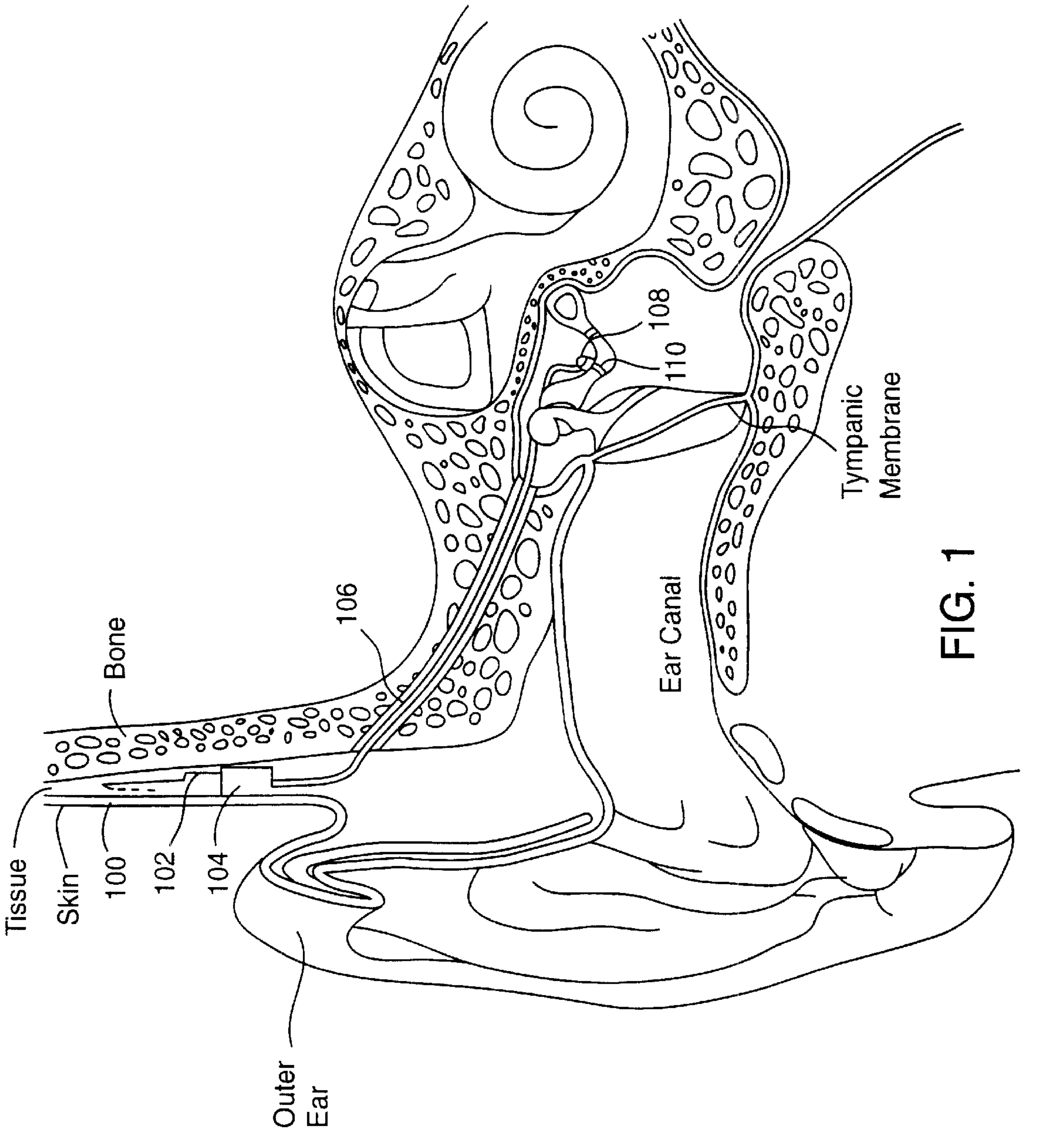
FIG. 1 shows a cross-sectional view of an implantable microphone in a hearing system.

In the description that follows, the present invention will be described in reference to hearing systems. The present invention, however, is not limited to any use or configuration. Therefore, the description the embodiments that follow is for purposes of illustration and not limitation. The same reference numerals will be utilized to indicate structures corresponding to similar structures.

FIG. 1 illustrates an embodiment of the present invention in a hearing system. An implantable microphone 100 is located under the skin and tissue behind the outer ear or concha. The implantable microphone picks up sounds through the skin and tissue. The sounds are then translated into electrical signals and carried by leads 102 to a signal processor 104 which may also be located under skin and tissue.

The signal processor 104 receives the electrical signals from the implantable microphone 100 and processes the electrical signals appropriate for the hearing system and individual. An exemplary signal processor may include a battery and signal processing circuitry on an integrated circuit. For example, the signal processor may amplify certain frequencies in order to compensate for the hearing loss of the hearing-impaired person and/or to compensate for characteristics of the hearing system.

Electrical signals from the signal processor 104 travel via leads 106 to a direct-drive hearing device 108. The leads may pass through a channel in the bone as shown or may run under the skin in the ear canal (not shown). In a preferred embodiment, the direct-drive hearing device is a Floating Mass Transducer (FMT) described in U.S. application Ser. No. 08/582,301, filed Jan. 3, 1996 by Geoffrey R. Ball et al., which is hereby incorporated by reference for all purposes.

The direct-drive hearing device vibrates in response to the electric signals and transfers the vibration to the malleus by direct attachment utilizing a clip 110. Although the direct-drive hearing device is shown attached to an ossicle, device 108 may be attached to any structure that allows vibrations to be generated in the inner ear. For example, the direct-drive hearing device may be attached to the tympanic membrane, ossicle, oval and round windows, skull, and within the inner ear. However, if the implantable microphone and direct-drive device are both anchored to bone of the skull, it may be advantageous isolate one of the devices to prevent feedback.

Figure 2A:
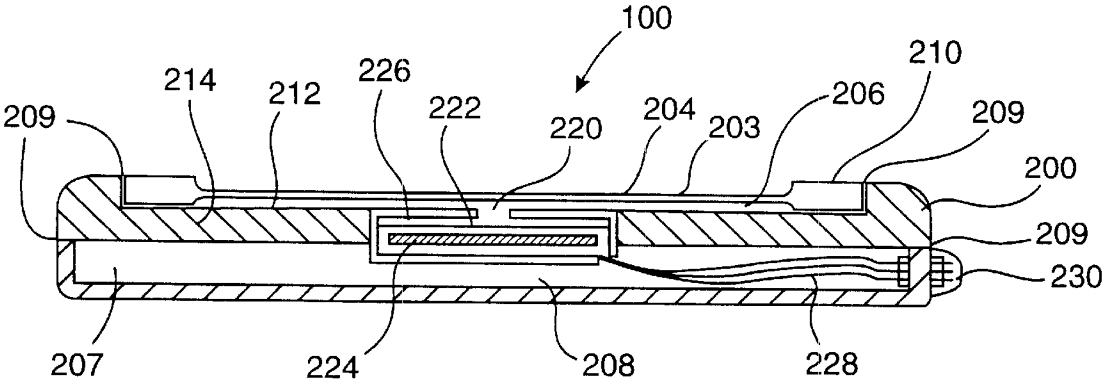
FIGS. 2A–2C show a cross-sectional view of an implantable microphone of the present invention.
Figure 2B:
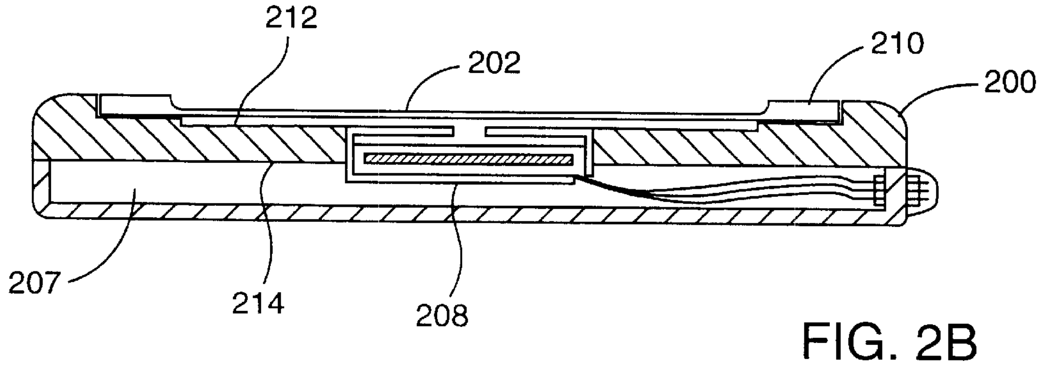
Figure 2C:
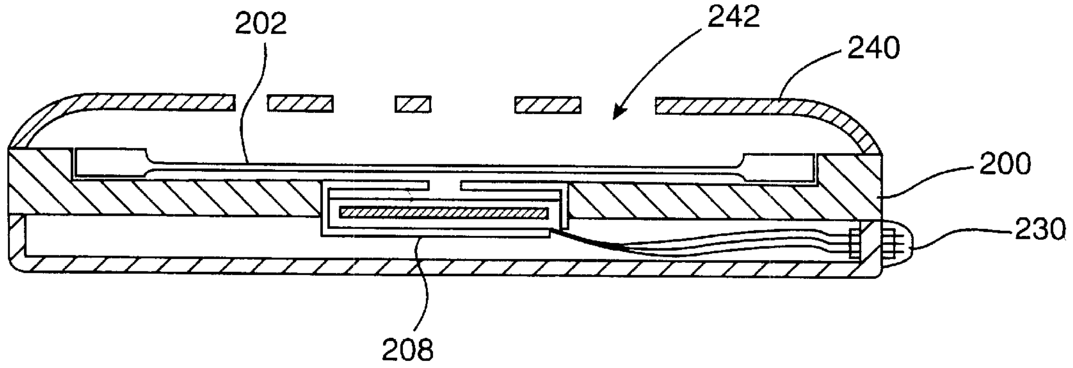

FIGS. 2A–2C show a cross-sectional view of an implantable microphone of the present invention. Typically, implantable microphone 100 is located under the skin and within the underlying tissue. In a preferred embodiment, the implantable microphone is placed against bone of the skull and may be attached to the bone (e.g., surgical screws). A shock absorbent material may be placed between the implantable microphone and the bone of the skull for vibration isolation. The shock absorbent material may include silicone or polyurethane.

The implantable microphone generally includes a housing 200, a microphone 208, and a membrane 202. The membrane flexes as it receives sounds transmitted through the skin and tissue. In a preferred embodiment, the membrane 202 and housing 200 both include titanium and are laser welded 209 together. In other embodiments, the housing 200 may include ceramic and the membrane 202 may include gold, platinum or stainless steel.

In order to optimize the response of the microphone, the membrane 202 must be sufficiently flexible. Increased membrane flexibility can be achieved, for example, by starting with a 0.0050" thick sheet of titanium (or other suitable material) and then chemically etching a circular portion of the sheet down to between 0.0005"–0.0020". Etching can be performed on one or both sides of the membrane 203, 204.

As a result, a circular band 210 of thicker (0.0050") titanium is left around the edges of the membrane. The thick band 210 provides stability to the membrane 202, and keeps the membrane in a flexible, unstressed or only slightly stressed state. The band 210 also provides for ease of attachment to the housing 200 at weld locations 209.

Preferably, the flexibility of the membrane 202 is defined in terms of the frequency response which it generates in open air, without an air cavity on either side. For example, the membrane will have a resonance frequency lower than 12,000 Hertz when measured by Laser Doppler Vibrometry. Resonance frequency measurements have been made with a Polytec Scanning Laser Doppler Vibrometer. In a preferred alternative, the flexibility of the membrane is defined as a function of its deflection when subjected to a force, centered on the membrane, supplied by a 3/32" diameter rod with a spherical tip. Force deflection measurements have been made with an Instron Tensile/Compression materials tester.

The membrane 202 disposed over the housing 200, defines a primary air cavity 206 therebetween. This cavity will typically be a hermetically sealed cavity necessitated by implantation into the body. Electro-acoustic simulation (lumped-parameter modeling), finite element analysis, and physical prototyping has shown that once the membrane is sufficiently flexible, the one variable that has a first order effect on frequency response is the acoustic compliance of this air cavity. Optimizing device response is accomplished by decreasing the acoustic compliance of this air cavity. Acoustic compliance is determined by the following equation:

$$C_A = V/\rho c^2 V/\gamma P_0$$

Where

V=volume of the air cavity

ρ=density of gas in the air cavity c=velocity of sound in the gas

γ=specific ratio of heats $P_0$=pressure of gas in air cavity

Preferably, the primary air cavity is defined as a volume that has an acoustic compliance of less than $4.3 \times 10^{-14}$ $m^5/N$ measured parametrically.

From the equation above it can be seen that a decrease in compliance may be obtained through a decrease in air cavity volume. Accordingly, in a preferred embodiment, the primary air cavity 206 has a very small volume. The depth of the primary air cavity, can range, for example, from 0.0005" to 0.0020". In a preferred embodiment, the primary air cavity may define a specific volume of no greater than 6 cubic millimeters (0.00036 $in^3$). The depth of the primary air cavity 206 may be accomplished by machining a specified depth into a surface of the housing 212 or by etching the membrane lower surface 204 directly opposite the housing 200, or a combination of both procedures.

The decrease in acoustic compliance can also be achieved by increasing the bulk modulus of the gas in the primary air cavity, equal to $\rho c^2$. This may be accomplished by increasing the pressure in the chamber, or by using a gas with a high density and velocity of sound, relative to air. Typical gases may include, for example, xenon, argon, helium, nitrogen, and the like.

In one embodiment, the microphone 208 is an electret microphone. It comprises a secondary air cavity 226, an electret membrane 222, a back plate 224, and an aperture or vent 220. An aperture 220 is connected to the primary air cavity 206 and allows vibrations of the membrane 202 to be transmitted as sound waves through the primary air cavity 206 and aperture 220 into the secondary air cavity 226. The sound waves passing through the secondary air cavity 226 generate vibrations on a surface of an electret membrane 222. The microphone, performs like a transducer, and subsequently transforms these vibrations into electrical signals. Since the response is driven by the characteristics of the primary air cavity 206, the characteristics of the electret microphone 208 can be adjusted to enhance overall microphone 100 response. In one embodiment, the aperture 220 acts as an acoustic resistance at the front end of the electret and is optimized such that the response peak of the response is damped, but overall sensitivity is minimally affected. This will create a flatter frequency response curve, and has been demonstrated with physical prototypes. In a preferred embodiment leads 228 carry the electrical signals from the microphone 208 to a direct-drive hearing device (FIG. 1) which vibrates in response to the electric signals and transfers the vibration to the malleus or other appropriate inner ear structure.

The typical implantable microphone 100 will include a rear chamber 207. The rear chamber 207 is suited for encasing the leads 228 which pass from the electret microphone 208. A hermetically sealed feedthrough 230 is included in the housing 200 which allows the leads 228 to exit the rear chamber.

In another embodiment, the implantable microphone 100 includes a protective cover 240. The protective cover protects the implantable microphone (and membrane) from damage when a user's head is struck with an object as may sometimes happens in contact sports. The protective cover 240 includes inlet ports 242 which allow sounds to travel to the membrane uninhibited. The protective cover 240 may include a number of materials including plastic, stainless steel, titanium, and is ceramic.

Figure 3:
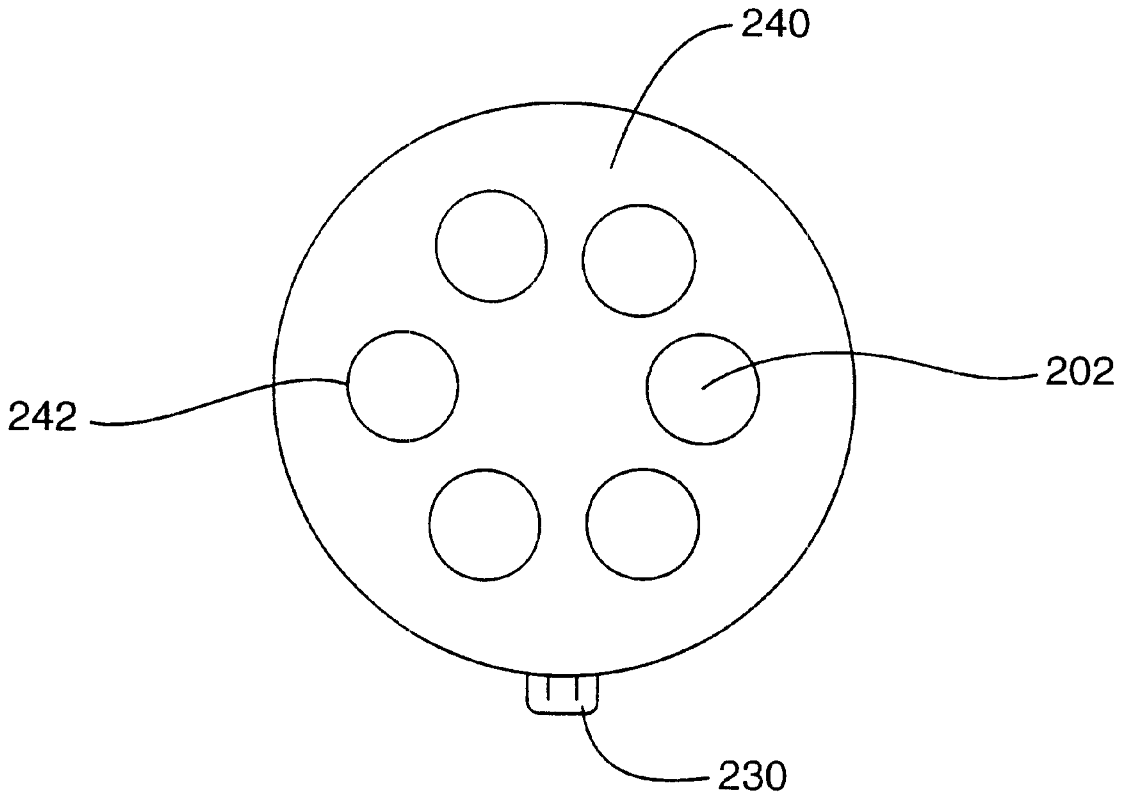
FIG. 3 shows a top view of a protective cover.

FIG. 3 shows a top view of a protective cover. As shown, protective cover 240 (and therefore the underlying membrane 202) is the majority of the top surface area of the implantable microphone. In this example, there are six inlet ports 242 through which sound may travel to the underlying membrane 202.

Figure 4A:
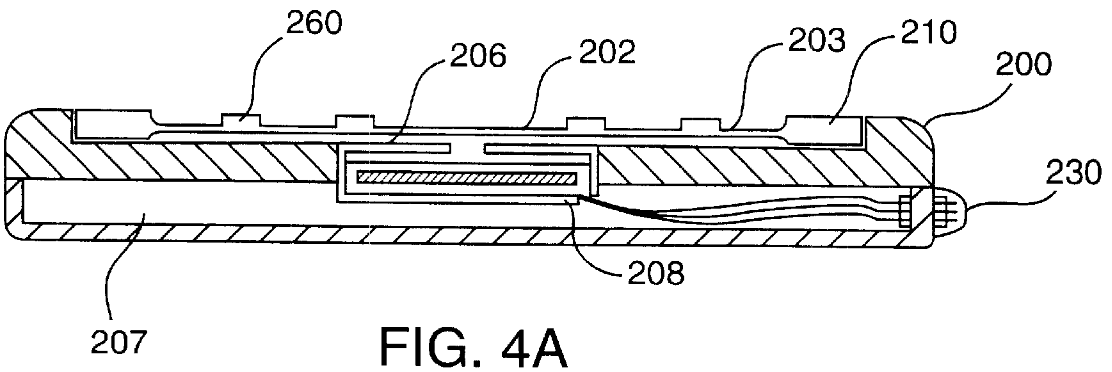
FIGS. 4A–4B show a cross-sectional view of an implantable microphone with compliance rings.
Figure 4B:
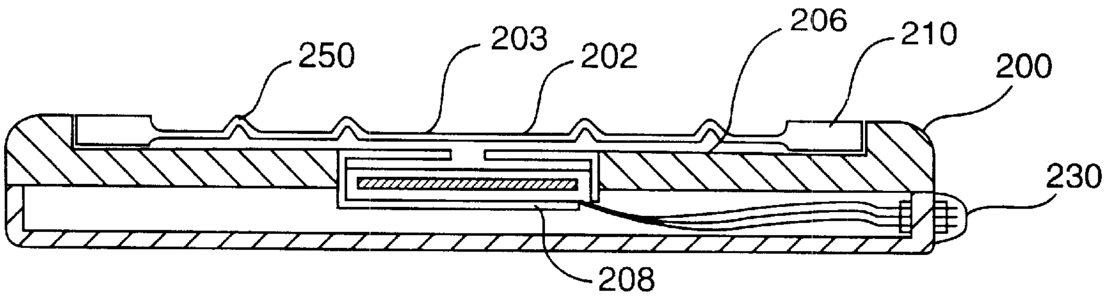
Figure 4C:
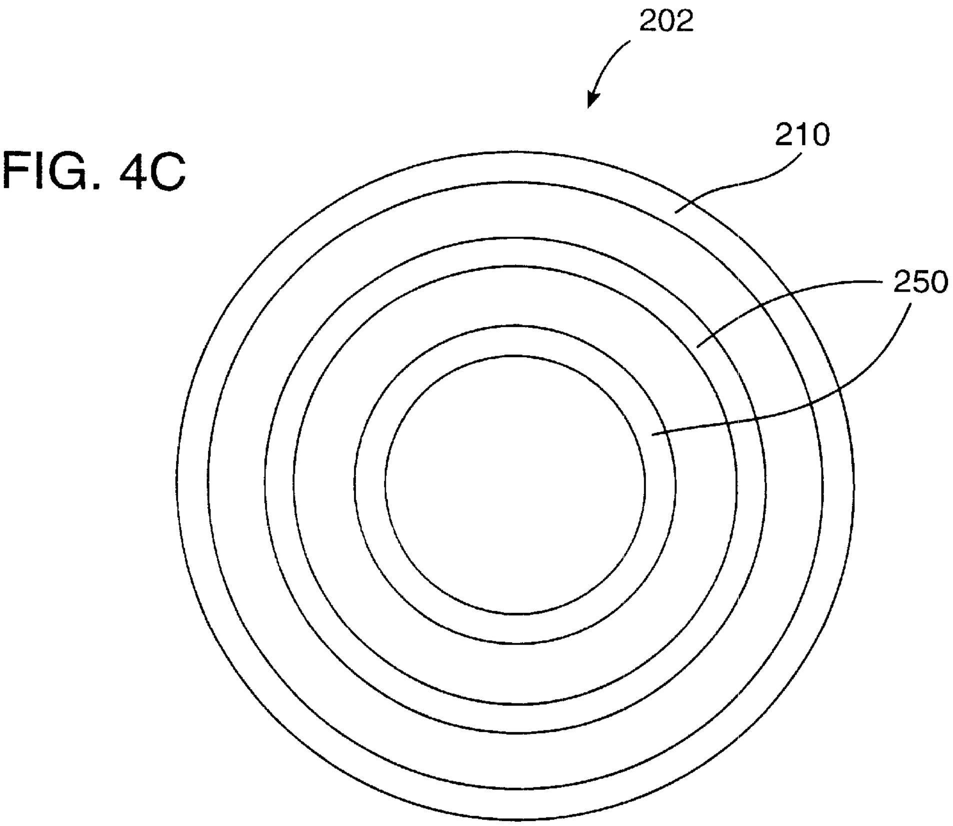
FIGS. 4C–4D show a top view of an implantable microphone with compliance rings.
Figure 4D:
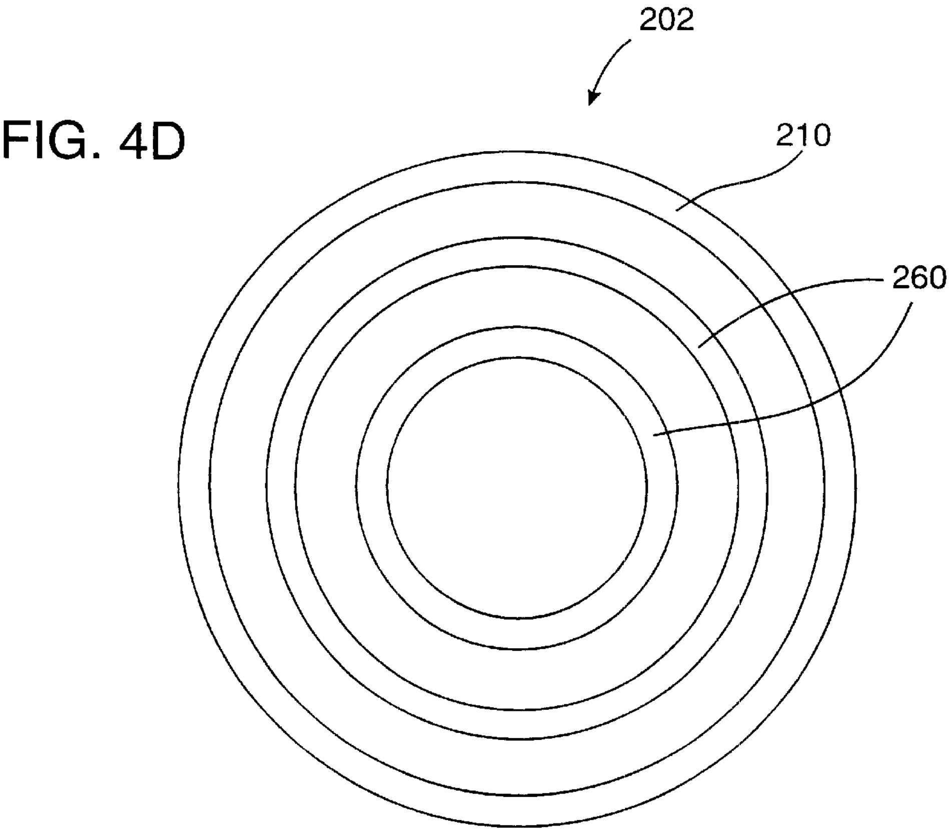

FIGS. 4A–4B show a cross-sectional view of an implantable microphone with compliance rings. In a preferred embodiment, the compliance rings are provided to ensure a smooth frequency response by creating a single node, piston-like displacement of the membrane. The compliance rings may be fabricated using two different methods. FIG. 4A shows a cross-sectional view of the membrane 202 that has been depth etched to form rings 260 having a rectangular cross-section. The cross-sectional shape of the rings 260 is a function of the manufacturing process (i.e. depth of etching). An alternative manufacturing process, shown in FIG. 4B, provides compliance rings 250 formed mechanically, for example, by stamping. These rings may provide additional flexibility to the membrane. FIGS. 4C and 4D show a top view of the membrane 202 and further show how the rings 250, 260 may be positioned on the membrane.

Figure 5A:
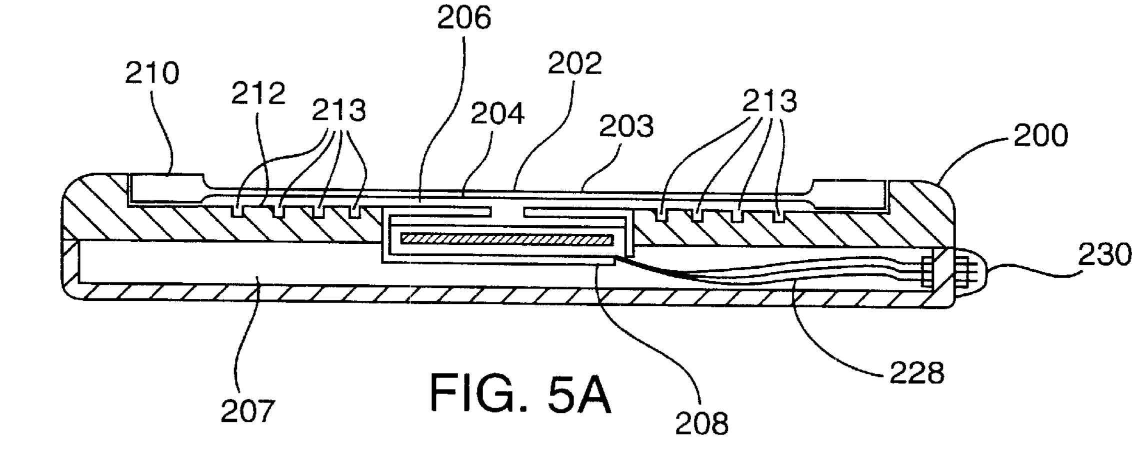
FIGS. 5A–5B show a cross-sectional view of an implantable microphone with an air cavity and surface details.
Figure 5B:
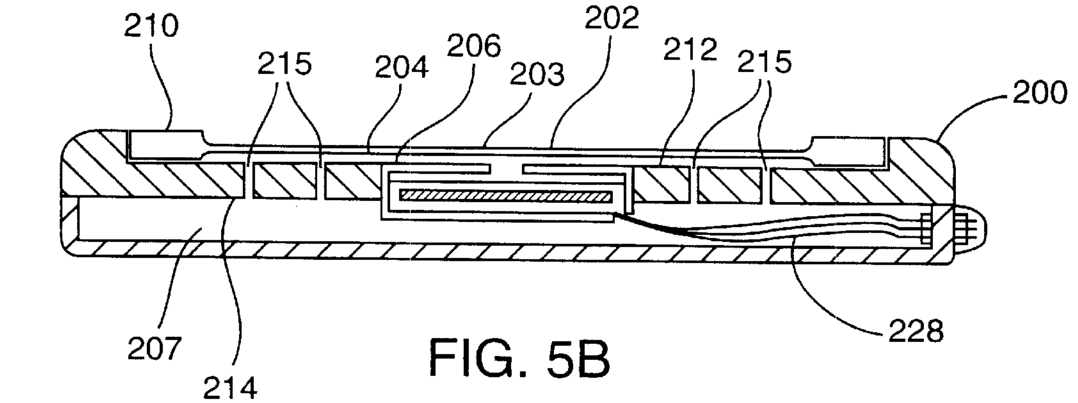

FIGS. 5A–5B show a cross-sectional view of an implantable microphone with a primary cavity and surface details. In another embodiment of the implantable microphone, a surface of the housing 212 immediately opposite the lower surface of the membrane 204 will have fabricated surface details such as pits or grooves 213. The pits or grooves 213 are configured such that peak resonance damping may be optimized. In yet another embodiment of this concept, the primary air cavity 206 will have at least one hole 215 which connects the primary air cavity 206 to the rear chamber 207. The result of the communication between the primary air cavity and the rear chamber is the formation of a resonance chamber for response shaping. The diameter of the hole or holes may, for example, be less than 0.020". Preferably, both cavities will remain hermetically sealed to the outside.

Figure 6:
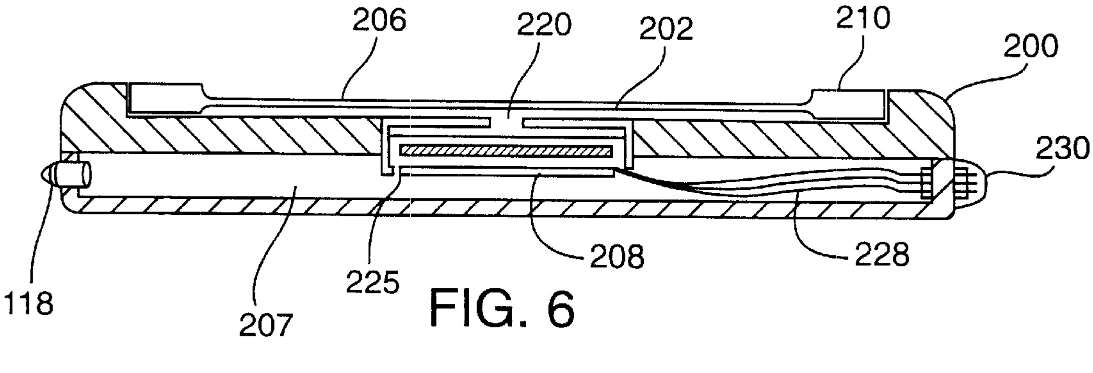
FIG. 6 shows a cross-sectional view of an implantable microphone with a vented electret microphone.

FIG. 6 shows a cross-sectional view of an implantable microphone with an internally vented microphone 208. The internally vented microphone is another embodiment of the present invention having a membrane 202, a housing 200, a microphone 208 and a rear chamber 207. In this embodiment, the microphone 208 comprises a secondary air cavity 226, an electret membrane 222, a back plate 224, an aperture 220 and a vent 225. The aperture 220 connects the secondary air cavity 226 to the primary air cavity 206 so that vibrations of the membrane are transmitted through the primary air cavity 206 through the aperture 220 to the secondary air cavity 226. A vent 225 is provided to connect the secondary air cavity 226 to the rear chamber 207. The rear chamber 207 encases the microphone leads 228. The portion of the housing 200 which surrounds the rear chamber further comprises a feedthrough 230 and a gas-fill device 118. The gas-fill device aids in filling the microphone 100 with specialty gases, such as Xenon. Because of the aperture 220 and vent 225, the gas is allowed to permeate the entire microphone device. Conversely, gas can be evacuated from the entire microphone device as well. The device 118 will be a hollow thin-walled tube which can be easily sealed using a crimp-induced cold weld or other similar means for sealing the tube. In another embodiment, the first surface of the housing 212 may have surface details, such as holes (FIG. 5B) which will also allow a gas to permeate from the rear chamber 207 to the primary cavity 206. In all instances it is preferred that the cavities within the device remain hermetically sealed from the outside.

Figure 7:
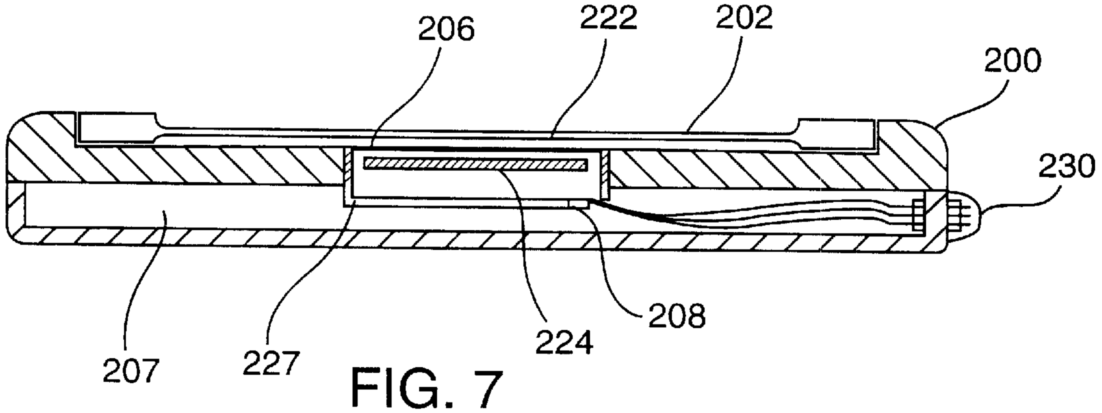
FIG. 7 shows a cross-sectional view of an implantable microphone with an exposed electret microphone.

FIG. 7 shows a cross-sectional view of an implantable microphone with an exposed electret microphone membrane. Another embodiment of the present invention provides an implantable microphone having a membrane 202, a housing 200, a microphone 208 and a rear chamber 207. The microphone 208, is an electret microphone, that has been modified such that the membrane 222 is directly exposed to the primary air cavity 206. This is accomplished by eliminating the top of the microphone protective cover 227, thus eliminating the aperture 220 and the secondary air cavity 226, as well. Exposing the electret membrane 222 directly to the primary air cavity 206 reduces the volume of the air cavity 206. Accordingly the acoustic compliance of the primary cavity is decreased and the performance may be improved.

Figure 8A:
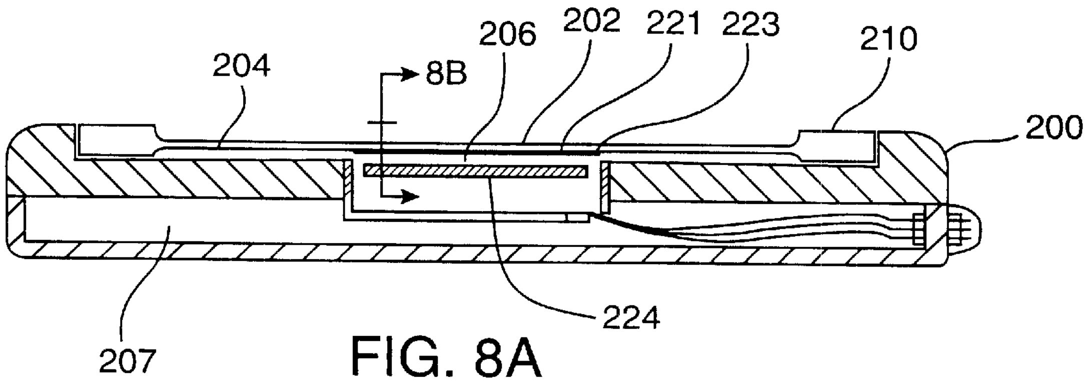
FIGS. 8A–8B shows a cross-sectional view of an implantable microphone with an electret microphone with no electret membrane and a cross-sectional view of the membrane of this embodiment, respectively.
Figure 8B:
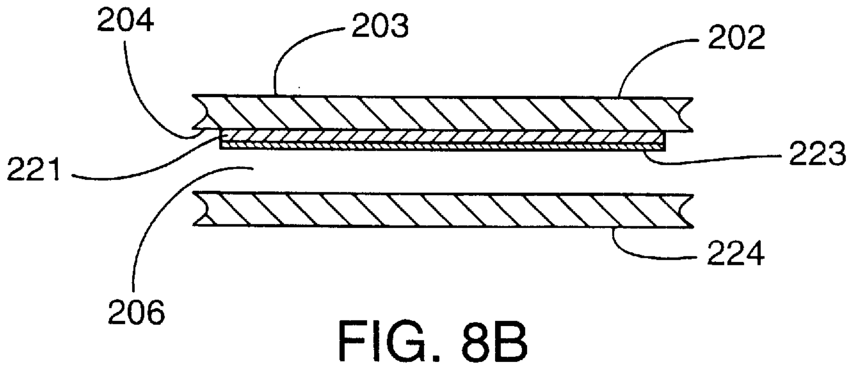

FIG. 8A shows a cross-sectional view of an implantable microphone with an electret microphone having no electret membrane. Another embodiment of the present invention, contains an electret microphone that has been modified such that the electret membrane 222 (See FIG. 7) is eliminated. The lower surface 204 of the membrane 202 has an insulation layer 221 secured directly on to the lower surface of the membrane 204. An electret membrane-type material 223 is placed directly onto the insulation layer 221. This material could be, for example, polyvinylidene fluoride (PVDF), Teflon® FEP, or single-side metallized mylar. FIG. 8B shows a cross section of the membrane 202 with the various layers attached. The backplate 224 is placed in close proximity to the PVDF layer 223 and is disposed within the air cavity. In this configuration, the membrane 202 will function as the membrane of the electret microphone. The primary air cavity volume 206 is considerably reduced which optimally decreases its acoustic compliance.

Figure 9:
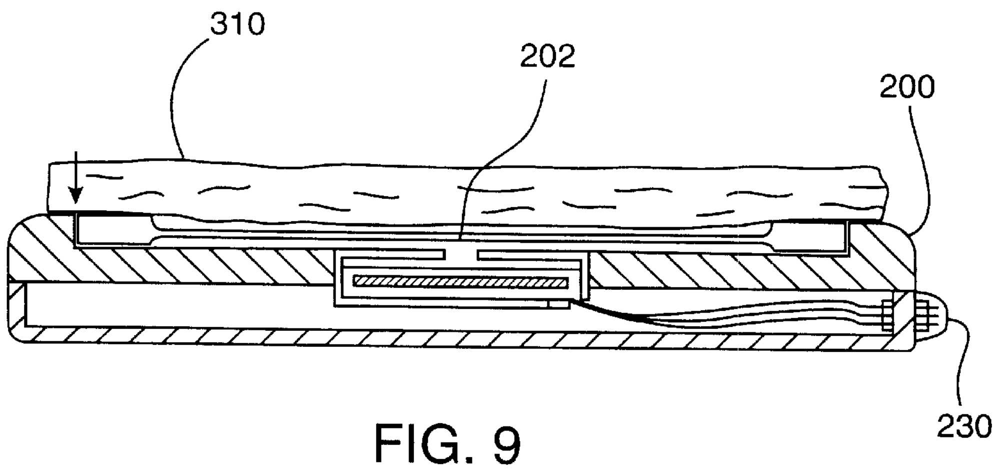
FIG. 9 shows a cross-sectional view of an implantable microphone with a biocompatible material.

FIG. 9 shows a cross-sectional view of an implantable microphone with a biocompatible material. Since the implantable microphone is to be received into the human body it may be coated with a protective biocompatible material. The coating (not shown) may be parylene or similar substance and will completely encapsulate the microphone to aid in biocompatability. In a preferred embodiment, a biodegradable material 310 may be placed directly in front of the membrane 202. In this configuration, the initial tissue growth that typically occurs after surgical implantation (the healing process) would not be allowed to impinge on the microphone membrane 202. Human tissue that impinges or adheres to the membrane 202 may affect its frequency response. Preferably, the material will degrade over time and be absorbed into the body. After the healing process is concluded, the volume of space occupied by the biodegradable material 310 will fill with body fluids. Biodegradable materials suitable for this embodiment include lactide and glycolide polymers. The materials may be held in place by the protective cover or made to adhere to the membrane surface.

Figure 10:
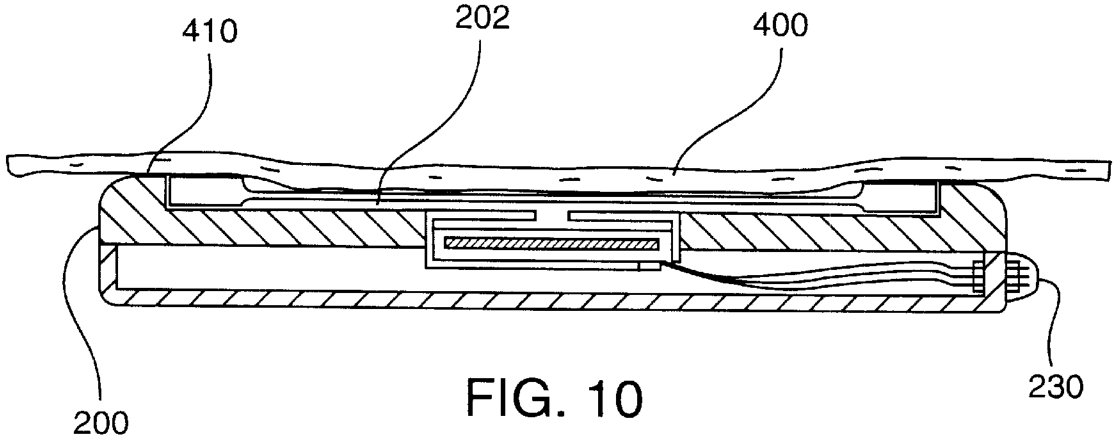
FIG. 10 shows a cross-sectional view of an implantable microphone with synthetic skin.

FIG. 10 shows a cross-sectional view of an implantable microphone with "synthetic skin". In another embodiment of the present invention, a synthetic skin 400 or similar material, is made to adhere 410 to the membrane 202. This patch 400 can be sewn to the edges of the skin of a patient, taking the place of the real skin removed by a surgeon. Placement could be anywhere on the side of the head, or it could be used in place of a tympanic membrane.

While the above is a complete description of preferred embodiments of the invention, various alternatives, modifications and equivalents may be used. It should be evident that the present invention is equally applicable by making appropriate modifications to the embodiments described above. For example, the above has shown that the implantable microphone and audio processor are separate; however, these two devices may be integrated into one device. Therefore, the above description should not be taken as limiting the scope of the invention which is defined by the metes and bounds of the appended claims along with their full scope of equivalents.

What is claimed is:

1. An implantable microphone device, comprising:

a housing;

a membrane comprising at least one compliance ring disposed over a surface of the housing to define a primary air cavity therebetween;

a microphone assembly secured on the housing and having an aperture open to the primary air cavity, the microphone having a secondary air cavity coupled to the primary air cavity through the aperture so that vibrations of the membrane are transmitted through the primary air cavity and aperture to the secondary air cavity; and a microphone transducer disposed in the secondary air cavity to detect said transmitted vibrations.

2. The device of claim 1, wherein the microphone transducer comprises an electret membrane, a backplate, and leads.

3. The device of claim 1, wherein the housing comprises a rear chamber.

4. The device of claim 3, wherein the housing further comprises a hermetic feedthrough for access to leads encased in the rear chamber and connected to the microphone assembly.

5. The device of claim 1, further comprising a protective cover over the membrane.

6. The device of claim 5, wherein the protective cover over the membrane is a perforated cover.

7. The device of claim 5, wherein the protective cover is a wire grid.

8. The device of claim 1, wherein the membrane is a substantially flexible membrane.

9. The device of claim 1, wherein the membrane has a free standing resonant frequency in air below 12,000 Hz.

10. The device of claim 1, wherein a peripheral portion of the membrane is substantially thicker than a center portion of the membrane.

11. The device of claim 10, wherein the center portion of the membrane is etched or formed to a thickness of between 0.0005 and 0.0025".

12. The device of claim 1, wherein the primary air cavity defines a volume that has an acoustic compliance of less than $4.3\times10^{-14}$ $m^5/N$.

13. The device of claim 1, wherein the primary air cavity defines a volume of less than 6 $mm^3$.

14. The device of claim 1, wherein the primary air cavity, includes a gas selected from the group consisting of argon, helium, xenon, nitrogen, and sulfur hexafluoride.

15. The device of claim 1, wherein the primary air cavity is hermetically sealed.

16. The device of claim 1, wherein the housing and membrane are composed of titanium.

17. The device of claim 16, wherein the membrane is laser or projection welded to the housing.

18. The device of claim 1, wherein the membrane deflects no less than 0.015" per pound over the range of 0.05 to 0.25 lbs when subjected to a centered force from a spherical tipped 3/32" rod.

19. The device of claim 1, wherein the device is completely encapsulated by a biocompatible material.

20. An implantable microphone device, comprising:

a housing having a surface;

a membrane disposed over the surface of the housing to define a primary air cavity therebetween;

surface details positioned on the surface of the housing;

a microphone assembly secured on the housing and having an aperture open to the primary air cavity, the microphone having a secondary air cavity coupled to the primary air cavity through the aperture so that vibrations of the membrane are transmitted through the primary air cavity and aperture to the secondary air cavity; and a microphone transducer disposed in the secondary air cavity to detect said transmitted vibrations.

21. The device of claim 20, wherein the housing comprises a rear chamber.

22. The device of claim 20, wherein the housing further comprises a hermetic feedthrough for access to leads encased in the rear chamber and connected to the microphone assembly.

23. The device of claim 20, wherein the surface details include pits or grooves.

24. The device of claim 21, wherein the surface details include at least one hole which connects the primary air cavity to the rear chamber.

25. The device of claim 20, further comprising a protective cover over the membrane.

26. The device of claim 25, wherein the protective cover over the membrane is a perforated cover.

27. The device of claim 20, wherein the membrane is a substantially flexible membrane.

28. The device of claim 20, wherein a peripheral portion of the membrane is substantially thicker than a center portion of the membrane.

29. The device of claim 28, wherein the center portion of the membrane is etched or formed to a thickness of between 0.0005" and 0.0025".

30. The device of claim 20, wherein the membrane comprises at least one compliance ring.

31. The device of claim 30, wherein the at least one compliance ring is either etched or formed.

32. The device of claim 20, wherein the primary air cavity, includes a gas selected from the group consisting of argon, helium, xenon, nitrogen, and sulfur hexafluoride.

33. The device of claim 20, wherein the housing and membrane are composed of titanium.

34. The device of claim 33, wherein the membrane is laser welded to the housing.

35. The device of claim 20, wherein the microphone transducer comprises an electret membrane, a backplate, and leads.

36. The device of claim 20, wherein the device is completely encapsulated by a biocompatible material.

37. An implantable microphone device, comprising:

a housing;

a membrane comprising at least one compliance ring disposed over a surface of the housing to define an air cavity therebetween; and a microphone assembly secured on the housing, the microphone assembly comprising a microphone transducer having an electret membrane, a backplate, and leads, the electret membrane being exposed to the air cavity.

38. The device of claim 37, further comprising a protective cover over the membrane.

39. The device of claim 38, wherein the protective cover over the membrane is a perforated cover.

40. The device of claim 37, wherein the housing comprises a rear chamber and a hermetic feedthrough for access to leads encased in the rear chamber and connected to the microphone assembly.

41. The device of claim 32, wherein the membrane is a substantially flexible membrane.

42. The device of claim 32, wherein the membrane has a free standing resonant frequency in air below 12,000 Hz.

43. The device of claim 32, wherein a peripheral portion of the membrane is substantially thicker than a center portion of the membrane.

44. The device of claim 43, wherein the center portion of the membrane is etched or formed to a thickness of between 0.0005" and 0.0025".

45. The device of claim 37, wherein the at least one compliance ring is either etched or formed.

46. The device of claim 37, wherein the primary air cavity defines a volume that has an acoustic compliance of less than $4.3\times10^{-14}$ $m^5/N$.

47. The device of claim 37, wherein the primary air cavity defines a volume of less than 6 $mm^3$.

48. The device of claim 37, wherein the primary air cavity, includes a gas selected from the group consisting of argon, helium, xenon, nitrogen, and sulfur hexafluoride.

49. The device of claim 37, wherein the membrane deflects no less than 0.015" per pound over the range of 0.05 to 0.25 lbs when subjected to a centered force from a spherical tipped 3/32" rod.

50. The device of claim 37, wherein the housing and membrane are composed of titanium.

51. The device of claim 50, wherein the membrane is laser or projection welded to the housing.

52. The device of claim 37, wherein the device is completely encapsulated by a biocompatible material.

* * * * *